United States Patent
Nguyen et al.

(10) Patent No.: US 8,329,918 B2
(45) Date of Patent: Dec. 11, 2012

(54) SELECTIVE ALPHA 2B/2C AGONISTS

(75) Inventors: Phong X. Nguyen, Placentia, CA (US); Ken Chow, Newport Coast, CA (US); Todd M. Heidelbaugh, Fountain Valley, CA (US); Dario G. Gomez, Rancho Santa Margarita, CA (US); Wenkui K. Fang, Irvine, CA (US); Santosh C. Sinha, Ladera Ranch, CA (US); Michael E. Garst, Newport Beach, CA (US); Daniel W. Gil, Corona Del Mar, CA (US)

(73) Assignee: Allergan Inc., Irvine, CA (US)

( * ) Notice: Subject to any disclaimer, the term of this patent is extended or adjusted under 35 U.S.C. 154(b) by 169 days.

(21) Appl. No.: 12/828,429

(22) Filed: Jul. 1, 2010

(65) Prior Publication Data

US 2011/0028523 A1 Feb. 3, 2011

Related U.S. Application Data

(60) Provisional application No. 61/229,910, filed on Jul. 30, 2009.

(51) Int. Cl.
*C07D 263/28* (2006.01)
*A61K 31/42* (2006.01)
(52) U.S. Cl. ........................ 548/233; 514/377
(58) Field of Classification Search .................. None
See application file for complete search history.

(56) References Cited

U.S. PATENT DOCUMENTS

| | | | |
|---|---|---|---|
| 7,655,600 B2 * | 2/2010 | Kordes et al. | 504/266 |
| 8,193,118 B2 * | 6/2012 | Dixson et al. | 504/101 |
| 2008/0153881 A1 | 6/2008 | Brooks | |
| 2011/0124647 A1 * | 5/2011 | Arnold et al. | 514/236.8 |
| 2012/0041031 A1 * | 2/2012 | Gil et al. | 514/340 |
| 2012/0083508 A1 * | 4/2012 | Gil et al. | 514/314 |

FOREIGN PATENT DOCUMENTS

| | | |
|---|---|---|
| WO | WO 92/00073 | 1/1992 |
| WO | WO 03/099289 | 12/2003 |
| WO | WO 2006/127426 A2 | 11/2006 |
| WO | WO 2008119511 A1 * | 10/2008 |

OTHER PUBLICATIONS

Rafaeli et al. Pesticide Biochemistry and Physiology vol. 65(3):194-204 (1999).*
Hirashima et al. Pesticide Biochemistry and Physiology vol. 58(3): 219-229 (1997).*
Hirashima A et al: "Three-Dimensional Molecular-Field Analyses of Octopaminergic Agonists for the Cockroach Neuronal Octopamine Receptor" Bioorganic and Medicinal Chemistry 20030815 GB LNKD-DOI:10.1016/S0968-0896(03)00313-4, vol. 11, No. 17, Aug. 15, 2003, pp. 3753-3760, XP002603296.
Messier; Pharmacol Toxicol; 76, pp. 308-311; 1995.

* cited by examiner

*Primary Examiner* — Kamal Saeed
*Assistant Examiner* — Nyeemah A Grazier
(74) *Attorney, Agent, or Firm* — Doina G. Ene; John E. Wurst; Allergan, Inc.

(57) ABSTRACT

Described herein are compounds useful as agonists of alpha 2B/2C receptors. Pharmaceutical compositions including the presently described compounds and methods of treatment of diseases and conditions with the presently described compounds also are disclosed.

2 Claims, No Drawings

SELECTIVE ALPHA 2B/2C AGONISTS

CROSS-REFERENCE TO RELATED APPLICATION

This application is based, and claims priority under 35 U.S.C. §120 to U.S. Provisional Patent Application No. 61/229,910 filed on Jul. 30, 2009, and which is incorporated herein by reference.

FIELD OF THE INVENTION

The present disclosure generally relates to compounds useful as selective alpha 2B/2C agonists.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, beta 1, and beta 2 subtypes. Functional differences between alpha 1 and alpha 2 receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the alpha 1 subtype was reported. The alpha 1/alpha 2 selectivity of this compound was disclosed as being significant because agonist stimulation of the alpha 2 receptors was said to inhibit secretion of epinephrine and norepinephrine, while antagonism of the alpha 2 receptor was said to increase secretion of these hormones. Thus, the use of non-selective alpha-adrenergic blockers, such as phenoxybenzamine and phentolamine, was said to be limited by their alpha 2 adrenergic receptor mediated induction of increased plasma catecholamine concentration and the attendant physiological sequelae (increased heart rate and smooth muscle contraction).

The cloning, sequencing and expression of alpha receptor subtypes from animal tissues has led to the subclassification of the alpha 1 adrenoreceptors into alpha 1A, alpha 1B, and alpha 1D. Similarly, the alpha 2 adrenoreceptors have also been classified alpha 2A, alpha 2B, and alpha 2C receptors. Each alpha 2 receptor subtype appears to exhibit its own pharmacological and tissue specificities. Compounds having a degree of specificity for one or more of these subtypes may be more specific therapeutic agents for a given indication than an alpha 2 receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha 2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

Activation of a response at different alpha subtype receptors results in different physiological responses. Thus, compounds which selectively or preferentially activate only one or some of the alpha receptors will be valuable pharmacological tools to probe further the functional role of different alpha 2 receptor subtypes.

SUMMARY

Described herein are compounds which are useful as alpha 2B/2C agonists and in treating a wide variety of disorders associated with modulation of alpha 2B/2C receptors. These compounds are useful for the treatment of mammals including humans with diseases and conditions that are alleviated by alpha 2B/2C modulation, and in particular use as alpha 2B/2C agonists. Further, pharmaceutically acceptable salts, hydrates, solvates, crystal forms and individual isomers, enantiomers, and diastereomers thereof of the compounds described herein are for treatment as described herein.

In one embodiment described herein, compounds are describe with the structure represented by Formula 1

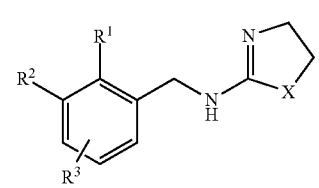

Formula 1 wherein:

$R^1$, $R^2$, and $R^3$ are same or different and each is H, $C_{1-4}$ alkyl, halogen, $CF_3$, OH, $OR^4$, CN, $N(R^5)2$, $CO_2R^5$, $CH_2OH$, or $C(O)N(R^5)_2$;

$R^4$ is $C_{1-4}$ alkyl, $CHF_2$, or $CF_3$;

$R^5$ is $C_{1-4}$ alkyl; and

X is O or S; or a pharmaceutically acceptable salt thereof.

In one example embodiment, $R^1$ is H, $C_{1-4}$ alkyl, halogen, or $OR^4$.

In another example embodiment, $R^2$ is H, $C_{1-4}$ alkyl, halogen, or $OR^4$.

In yet another example embodiment, $R^3$ is H or halogen.

In yet another example embodiment, X is S.

In yet another example embodiment, X is O.

In yet another example embodiment, $R^1=R^2=$H, $C_{1-4}$ alkyl, halogen, or $OR^4$;

$R^3$ is H or halogen; and

X is S or O.

In yet another example embodiment, the compound is:
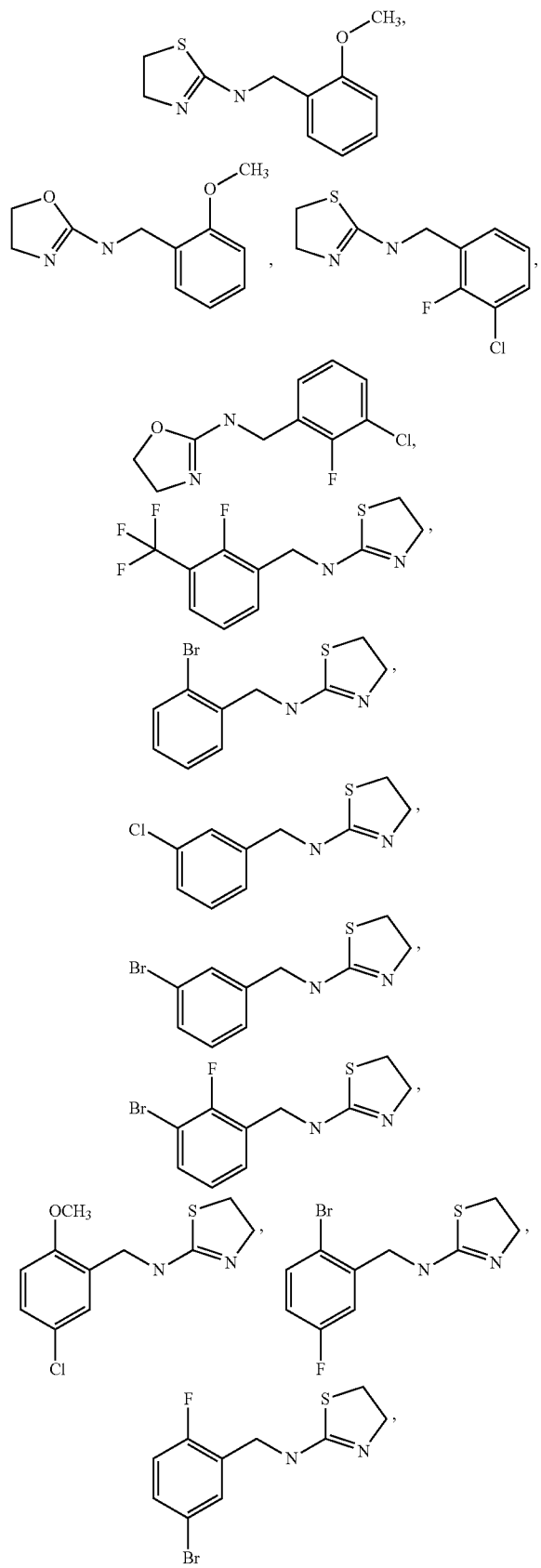
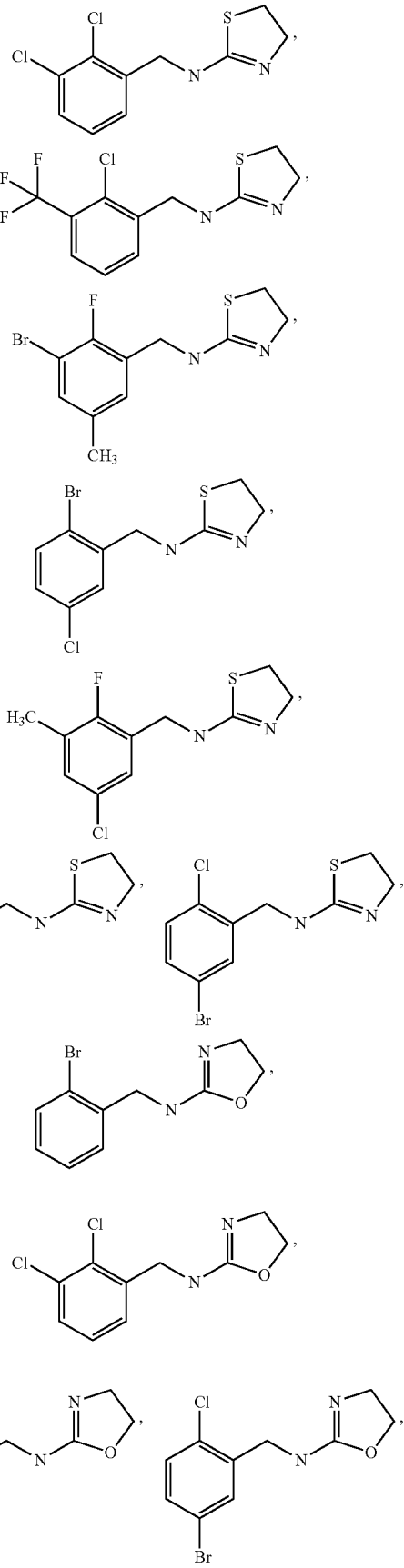

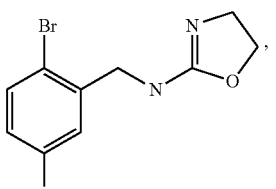
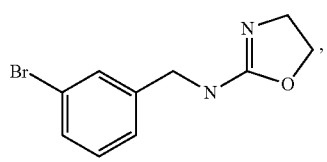
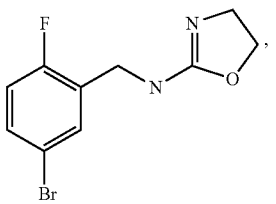
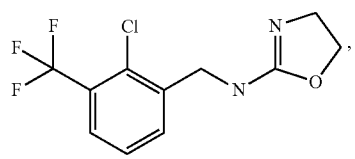
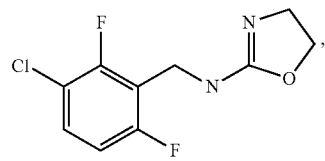
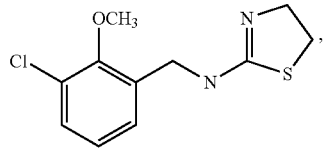
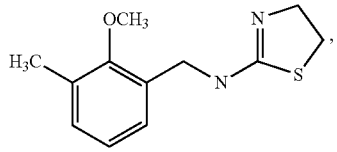
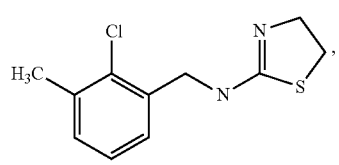
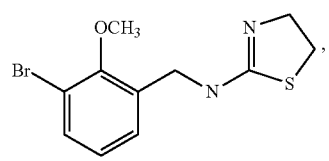
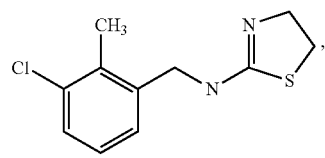
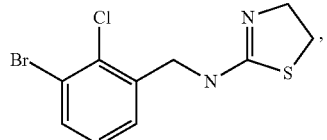
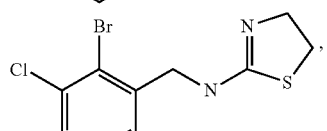
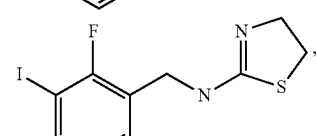
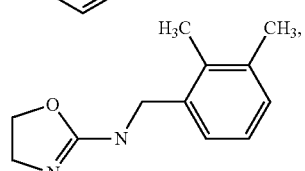
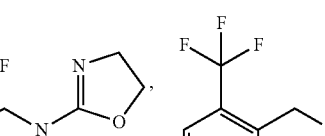
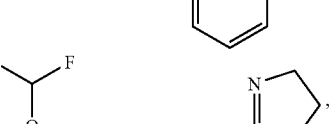
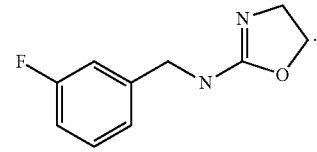

Also described are pharmaceutical compositions comprising a compound as described herein. Further described are methods for treating diseases and conditions using the compounds described herein, wherein the diseases and conditions are selected from the group consisting of glaucoma, elevated intraocular pressure, ischemic neuropathy, optic neuropathy, chronic pain, visceral pain, corneal pain, headache pain, migraine, cancer pain, back pain, post-herpetic neuralgia pain, fibromyalgia, allodynia, irritable bowel syndrome pain, muscle pain, diabetic neuropathy pain, diabetic retinopathy, retinal degenerative condition, stroke, cognitive deficit, neuropsychiatric condition, drug dependence, obsessive-compulsive disorder, obesity, insulin resistance, stress-related condition, diarrhea, diuresis, nasal congestion, spasticity, attention deficit disorder, psychoses, anxiety, depression, autoimmune disease, Crohn's disease, gastritis, Alzheimer's disease, Parkinson's ALS, and neurodegerative disease.

Definition of Terms

Certain terms as used in the specification are intended to refer to the following definitions, as detailed below. Where the definition of terms departs from the commonly used meaning of the term, applicant intends to utilize the definitions provided below, unless specifically indicated.

As used herein, "alkyl" refers to straight, branched chain or cyclic hydrocarbyl groups having from 1 to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. As used herein, "substituted alkyl" refers to alkyl moieties bearing substituents typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)$R^6$), alkoxymethyl, mercapto (—S—$R^6$), sulfoxy (—S(O)—$R^6$), sulfonyl (—S(O)$_2$—$R^6$), sulfonamide (—S(O)$_2$N($R^6$)$_2$), carbonate (—C(O)—O—$R^6$), oxyacyl (—OC(O)—$R^6$), carboxyl (—C(O)OH), ester (—C(O)O$R^6$), carbamate (—OC(O)—N($R^6$)$_2$), wherein $R^6$ is H or lower alkyl, lower alkenyl, lower alkynyl, aryl, heteroaryl, heterocycle, and the like. As used herein, "lower alkyl" refers to alkyl moieties having from 1 to about 6 carbon atoms.

As used herein, "alkenyl" refers to straight, branched chain or cyclic hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 1 to about 6 carbon atoms.

As used herein, "alkylacyl" refers to an alkyl ketone such as ethanone, propanone, and the like.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "aryl" refers to aromatic groups having in the range of 6 up to 14 carbon atoms and "substituted aryl" refers to aryl groups further bearing one or more substituents as set forth above.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "halogen" or "halide" refers to fluoride, chloride, bromide or iodide. The terms "fluoro", "chloro", "bromo", and "iodo" may also be used when referring to halogenated substituents, for example, "trifluoromethyl."

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents as set forth above.

As used herein, "heterocyclic" or "heterocycle" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" or "substituted heterocycle" refers to heterocyclic groups or heterocycles further bearing one or more substituents as set forth above.

As used herein, "hydroxyalkyl" refers to alkyl-OH, such as hydroxymethyl, hydroxyethyl, and the like.

As used herein, "pharmaceutically acceptable salt" refers to any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Further, pharmaceutically acceptable salt refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

As used herein "prodrug" refers to a compound which is converted to a therapeutically active compound after administration, and the term should be interpreted as broadly herein as is generally understood in the art. While not intending to limit the scope of the present description, conversion may occur by hydrolysis of an ester group or some other biologically labile group. Generally, but not necessarily, a prodrug is inactive or less active than the therapeutically active compound to which it is converted. Ester prodrugs of the compounds disclosed herein are contemplated. An ester may be derived from a carboxylic acid of $C_1$ (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

DETAILED DESCRIPTION

Described herein are compounds which are useful as alpha 2B/2C agonists and as a result are useful in treating a wide variety of disorders associated with modulation of alpha 2B/2C receptors. These compounds are useful for the treatment of mammals including humans with diseases and conditions that are alleviated by alpha 2B/2C modulation, and in particular use as alpha 2B/2C agonists.

In one embodiment described herein, compounds are describe with the structure represented by Formula 1

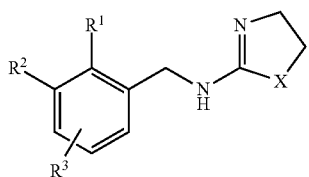

Formula 1 wherein:
$R^1$, $R^2$, and $R^3$ are same or different and each is H, $C_{1-4}$ alkyl, halogen, $CF_3$, OH, $OR^4$, CN, $N(R^5)_2$, $CO_2R^5$, $CH_2OH$, or $C(O)N(R^5)_2$;
$R^4$ is $C_{1-4}$ alkyl, $CHF_2$, or $CF_3$;
$R^5$ is $C_{1-4}$ alkyl; and
X is O or S; or a pharmaceutically acceptable salt thereof.

In one example embodiment, $R^1$ is H, $C_{1-4}$ alkyl, halogen, or $OR^4$.

In another example embodiment, $R^2$ is H, $C_{1-4}$ alkyl, halogen, or $OR^4$.

In yet another example embodiment, $R^3$ is H or halogen.
In yet another example embodiment, X is S.
In yet another example embodiment, X is O.
In yet another example embodiment, $R^1=R^2=$H, $C_{1-4}$ alkyl, halogen, or $OR^4$;
$R^3$ is H or halogen; and
X is S or O.

Further, pharmaceutically acceptable salts, hydrates, solvates, crystal forms and individual isomers, enantiomers, and diastereomers thereof of the compounds described herein are for treatment as described herein.

Some example compounds include:

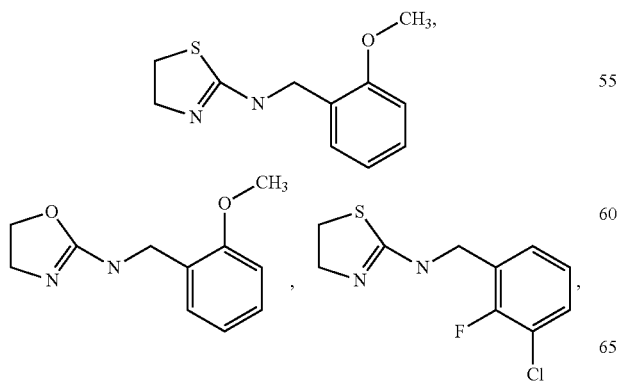

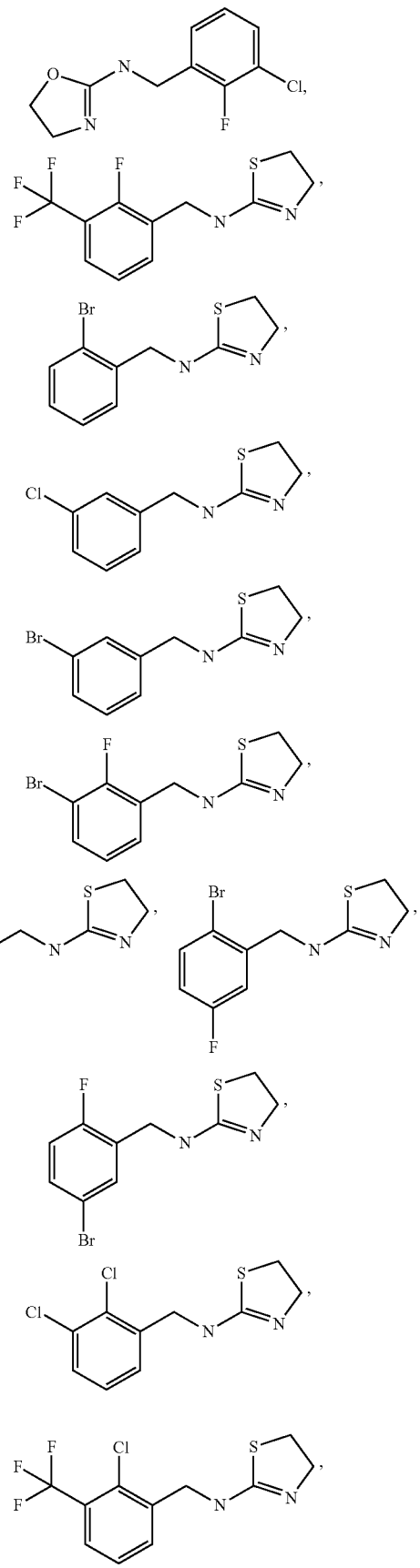

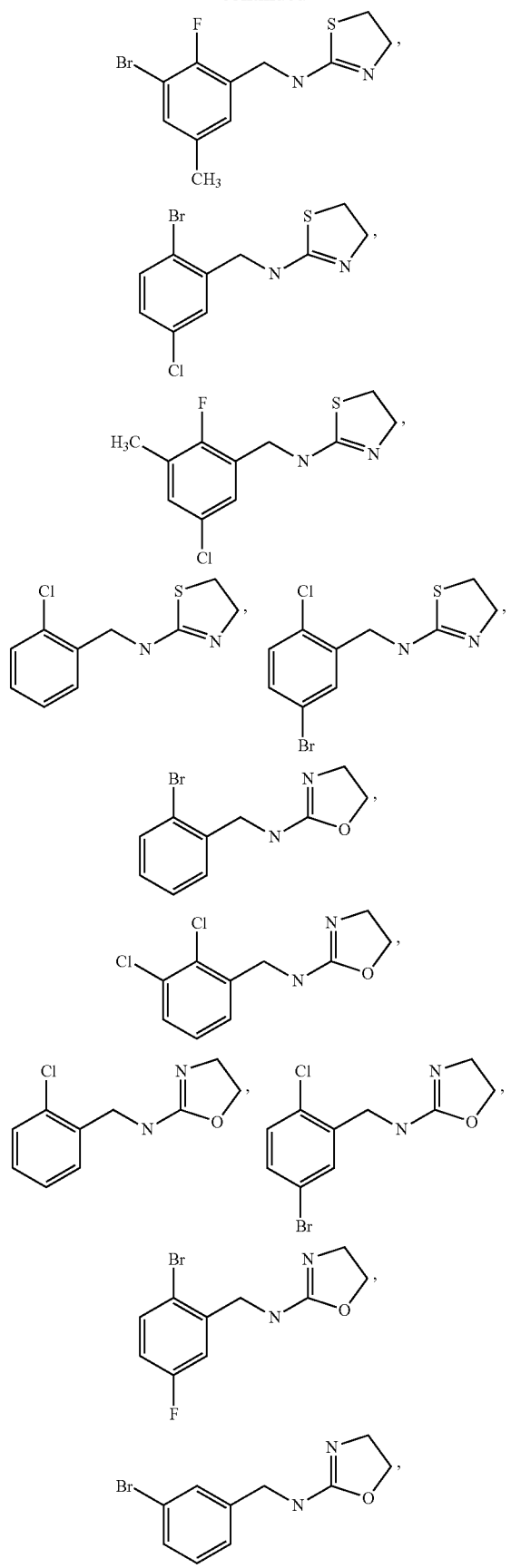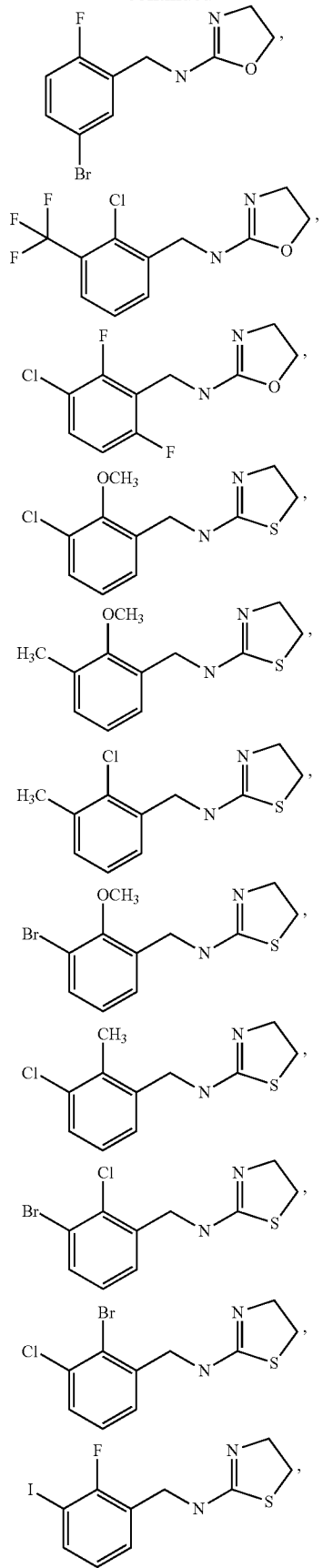

-continued

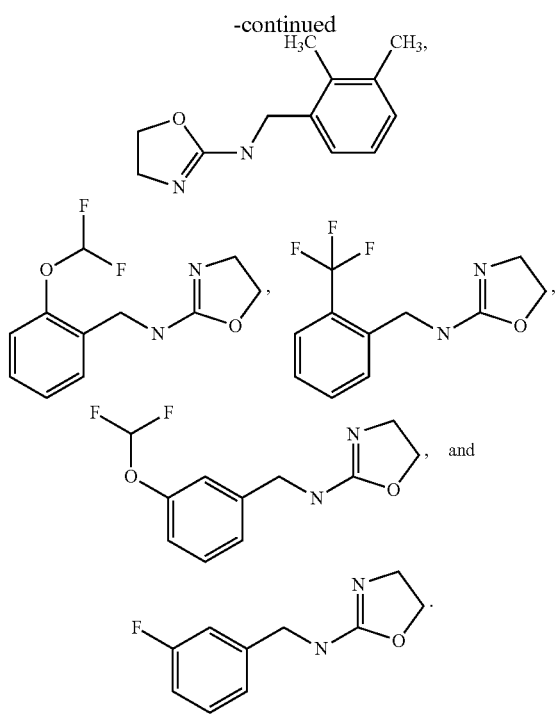

The compounds and pharmaceutical compositions described herein are useful as medicaments in mammals, including humans, for treatment of diseases and/or alleviations of conditions which are responsive to treatment by agonists of alpha 2B/2C receptors. Thus, in further example embodiments, there are provided methods for treating a disease or condition associated with modulation of alpha 2B/2C receptors. Such methods can be performed, for example, by administering to a subject in need thereof a pharmaceutical composition containing a therapeutically effective amount of at least one compound as described herein. The compounds described herein are useful for the treatment of mammals, including humans, with a wide range of diseases and conditions alleviated by alpha 2B/2C modulation. These diseases and conditions include, but are not limited to, glaucoma, elevated intraocular pressure, ischemic neuropathy, optic neuropathy, chronic pain, visceral pain, corneal pain, headache pain, migraine, cancer pain, back pain, post-herpetic neuralgia pain, fibromyalgia, allodynia, irritable bowel syndrome pain, muscle pain, diabetic neuropathy pain, diabetic retinopathy, retinal degenerative condition, stroke, cognitive deficit, neuropsychiatric condition, drug dependence, obsessive-compulsive disorder, obesity, insulin resistance, stress-related condition, diarrhea, diuresis, nasal congestion, spasticity, attention deficit disorder, psychoses, anxiety, depression, autoimmune disease, Crohn's disease, gastritis, Alzheimer's disease, Parkinson's ALS, and neurodegerative disease. In one embodiment, the diseases and conditions include chronic pain, neuropathic pain, visceral pain, fibromyalgia, allodynia, neuritis, Guillan-Barre syndrome, rheumatoid arthritis, type I diabetes, multiple sclerosis, graft-versus-host disease, autoimmune uveitis, ocular inflammation, dry eye disease, atopic dermatitis, psoriasis, inflammatory bowel disease, asthma, and aplastic anemia.

The compounds described herein may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. In another example embodiment, the compound or compounds may be present in a composition in a range of about 0.5 or about 1 to about 100 mg/kg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Both acute pain and chronic pain may be treated by administration of the compounds and compositions described herein. By "acute pain" is meant immediate, usually high threshold, pain brought about by injury such as a cut, crush, burn, or by chemical stimulation such as that experienced upon exposure to capsaicin, the active ingredient in chili peppers. By "chronic pain" is meant pain other than acute pain, such as, without limitation, neuropathic pain, visceral pain (including that brought about by Crohn's disease and irritable bowel syndrome, and referred pain.

Preferably, the patient will be administered a compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

In another embodiment, provided are pharmaceutical compositions including at least one compound in a pharmaceutically acceptable carrier. The phrase "pharmaceutically acceptable" means the carrier, diluent or excipient must be compatible with the other ingredients of the formulation and not deleterious to the recipient thereof.

Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Compounds described herein are included in pharmaceutical compositions in an amount sufficient to produce the desired effect upon the process or disease condition.

Pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may also be in the form of a sterile injectable suspension. Suspensions may be formulated according to known methods using suitable dispersing or wetting agents and suspending agents. The sterile injectable preparations may also be sterile injectable solutions or suspensions in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds described herein may also be administered in the form of suppositories for rectal administration. These compositions may be prepared by mixing the compounds with a suitable non-irritating excipient, such as cocoa butter, synthetic glyceride esters of polyethylene glycols, which are solid at ordinary temperatures, but liquefy and/or dissolve in the rectal cavity to release the drug.

The compounds described herein can also be administered as an ophthalmic ally acceptable formulation or composition. A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in ophthalmic compositions described herein include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In one example embodiment, an ophthalmic composition as described herein may have ingredients used in the following amounts listed in Table 1.

TABLE 1

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Since individual subjects may present a wide variation in severity of symptoms and each composition has its unique therapeutic characteristics, precise modes of administration and dosages employed for each subject is left to the discretion of a practitioner

EXAMPLE 1

General Synthesis A

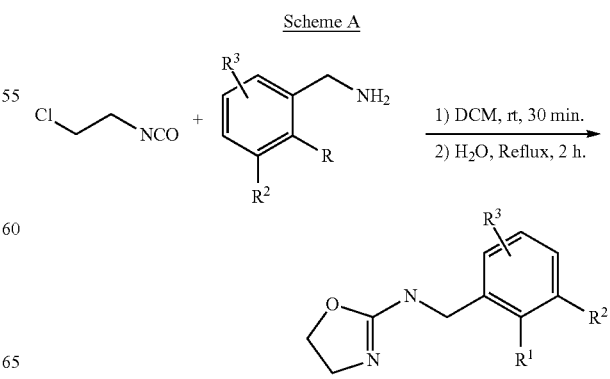

Scheme A depicts a general method for obtaining N-(Substituted benzyl)-4,5-dihydro-oxazol-2-amines.

EXAMPLE 1A

Synthesis of N-(2-methoxybenzyl)-4,5-dihydrooxazol-2-amine

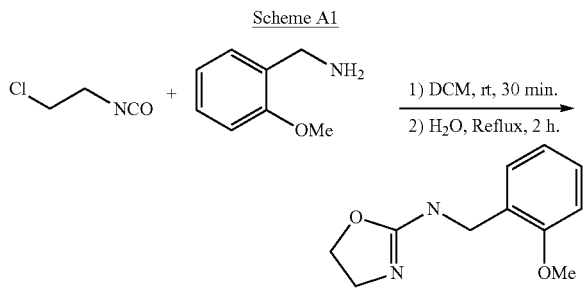

Scheme A1

Scheme A1 depicts a method for the preparation of N-(2-methoxybenzyl)-4,5-dihydrooxazol-2-amine.

Commercially available 2-chloroethylisocyanate (3.10 mL, 36.45 mmol) was added slowly to a solution of 2-methoxybenzylamine (5.00 mL, 36.45 mmol) in dichloromethane (60 mL) at room temperature. The resulting reaction mixture was stirred for 30 minutes and the intermediate product thus formed was filtered and washed with hexane, and then suspended in water (150 mL). This suspension was heated to reflux and stirred at refluxing for 2 hours, then cooled to room temperature. The reaction mixture was extracted with ethyl acetate, and the aqueous phase was basified with ammonium hydroxide to pH=14. The basified aqueous phase was then extracted with ethyl ether (50 mL) 3 times and the combined organic phases were dried with magnesium sulfate. Concentration gave 5.10 g of N-(2-methoxybenzyl)-4,5-dihydrooxazol-2-amine. Spectroscopic data: $^1$H NMR (300 MHz, CDCl$_3$) δ=3.80 (t, 2H, J=10.1 Hz), 3.85 (s, 3H), 4.26 (t, 2H, J=10.1 Hz), 4.38 (s, 2H), 6.83-6.95 (m, 2H), 7.20-7.32 (m, 2H).

The following compounds were prepared according to the method of Scheme A:

N-(3-chloro-2-fluorobenzyl)-4,5-dihydrooxazol-2-amine: $^1$H NMR (300 MHz, DMSO-d$^6$) δ=ppm 3.55 (t, J=8.35 Hz, 2 H), 4.16 (t, J=8.50 Hz, 2 H), 4.31 (s, 2 H), 7.15 (t, J=7.91 Hz, 1 H), 7.28-7.50 (m, 2 H).

N-(2-(difluoromethoxy)benzyl)-4,5-dihydrooxazol-2-amine: $^1$H NMR (300 MHz, CD$_3$OD) δ=ppm 3.68 (t, J=8.50 Hz, 2 H) 4.30 (t, J=8.50 Hz, 2 H) 4.37 (s, 2 H) 6.81 (t, J=74.17 Hz, 1 H) 7.09-7.25 (m, 2 H) 7.25-7.34 (m, 1 H) 7.40 (d, J=5.86 Hz, 1 H).

N-(2,3-dimethylbenzyl)-4,5-dihydrooxazol-2-amine: $^1$H NMR (300 MHz, CD$_3$OD) δ=ppm 2.21 (s, 3 H) 2.27 (s, 3 H) 3.64-3.79 (m, 2 H) 4.24-4.36 (m, 4 H) 6.96-7.15 (m, 3 H).

N-(2-(trifluoromethyl)benzyl)-4,5-dihydrooxazol-2-amine: $^1$H NMR (300 MHz, CD$_3$OD) δ=ppm 3.70 (t, J=8.50 Hz, 2 H) 4.32 (t, J=8.65 Hz, 2 H) 4.53 (s, 2 H) 7.37-7.46 (m, 1 H) 7.53-7.63 (m, 2 H) 7.67 (d, J=7.62 Hz, 1 H).

N-(3-(difluoromethoxy)benzyl)-4,5-dihydrooxazol-2-amine: $^1$H NMR (500 MHz, CD$_3$OD) δ ppm 3.70 (t, J=8.56 Hz, 2 H) 4.26-4.35 (m, 4 H) 6.79 (t, J=74.34 Hz, 1 H) 7.01 (dd, J=8.19, 2.08 Hz, 1 H) 7.09 (s, 1 H) 7.17 (d, J=7.58 Hz, 1 H) 7.34 (t, J=7.95 Hz, 1 H).

N-(3-fluorobenzyl)-4,5-dihydrooxazol-2-amine: $^1$H NMR (300 MHz, CDCl$_3$) δ ppm 3.77 (t, J=8.50 Hz, 2 H) 4.28 (t, J=8.50 Hz, 2 H) 4.38 (s, 2 H) 6.88-7.11 (m, 3H) 7.22-7.33 (m, 2 H).

N-(2-Bromobenzyl)-4,5-dihydrooxazol-2-amine: $^1$H NMR (300 MHz, CDCl$_3$) δ=ppm 3.80 (t, J=8.55 Hz, 2 H), 4.23-4.33 (m, 2 H), 4.48 (s, 2 H), 7.15 (td, J=7.66, 1.68 Hz, 1 H), 7.29-7.34 (m, 1 H), 7.44 (dd, J=7.62, 1.47 Hz, 1 H), 7.55 (dd, J=7.91, 1.03 Hz, 1 H).

N-(2-Chlorobenzyl)-4,5-dihydrooxazol-2-amine: $^1$H NMR (500 MHz, CDCl$_3$) δ ppm 3.79 (t, J=8.54 Hz, 2 H), 4.29 (t, J=8.60 Hz, 2 H), 4.49 (s, 2 H), 7.20-7.26 (m, 2H), 7.36 (dd, J=7.51, 1.65 Hz, 1 H), 7.43 (dd, J=7.32, 1.83 Hz, 1 H).

N-(5-Bromo-2-chlorobenzyl)-4,5-dihydrooxazol-2-amine: $^1$H NMR (300 MHz, CDCl$_3$) δ=ppm 3.81 (t, J=8.57 Hz, 2 H), 4.32 (t, J=8.57 Hz, 2 H), 4.47 (s, 2 H), 7.19-7.25 (m, 1 H), 7.31-7.38 (m, 1 H), 7.58 (d, J=2.20, 1 H).

N-(5-Bromo-2-fluorobenzyl)-4,5-dihydrooxazol-2-amine: $^1$H NMR (500 MHz, CDCl$_3$) δ ppm 3.77 (t, J=8.54 Hz, 2 H), 4.29 (t, J=8.54 Hz, 2 H), 4.41 (s, 2 H), 6.91 (t, J=9.09 Hz, 1 H), 7.34 (ddd, J=8.63, 4.55, 2.56 Hz, 1 H), 7.52 (dd, J=6.59, 2.56 Hz, 1H).

N-(2-Chloro-3-trifluoromethylbenzyl)-4,5-dihydrooxazol-2-amine: $^1$H NMR (300 MHz, CDCl$_3$) δ=ppm 3.77 (t, J=8.55 Hz, 2 H), 4.22-4.37 (m, 2 H), 4.54 (s, 2 H), 7.35 (t, J=7.73 Hz, 1 H), 7.58-7.69 (m, 2 H).

N-(3-Chloro-2,6-difluorobenzyl)-4,5-dihydrooxazol-2-amine: $^1$H NMR (500 MHz, CDCl$_3$ δ=ppm 3.76 (t, 2 H), 4.27 (t, J=8.54 Hz, 2 H), 4.49 (s, 2 H), 6.87 (td, J=8.76, 1.77 Hz, 1 H), 7.31 (td, J=8.54, 5.74 Hz, 1 H).

N-(2,3-Dichlorobenzyl)-4,5-dihydrooxazol-2-amine: $^1$H NMR (500 MHz, DMSO-d$^6$) δ=ppm 3.75 (t, 2 H), 4.50 (s, 2 H), 4.60 (t, J=8.30 Hz, 2 H), 6.57 (s, 4 H), 7.39 (d, J=4.88 Hz, 2 H), 7.58-7.63 (m, 1 H).

N-(2-Bromo-5-fluorobenzyl)-4,5-dihydrooxazol-2-amine: $^1$H NMR (300 MHz, CDCl$_3$) δ=ppm 3.80 (t, J=8.50 Hz, 2 H), 4.24-4.38 (m, 2 H), 4.44 (s, 2 H), 6.87 (td, J=8.28, 3.08 Hz, 1 H), 7.19 (dd, J=9.38, 2.93 Hz, 1 H), 7.49 (dd, J=8.72, 5.20 Hz, 1 H).

EXAMPLE 2

General Synthesis B

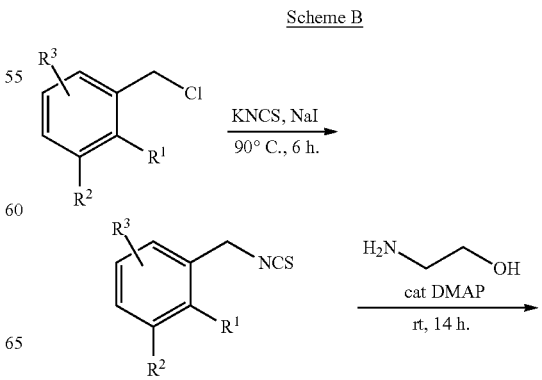

Scheme B

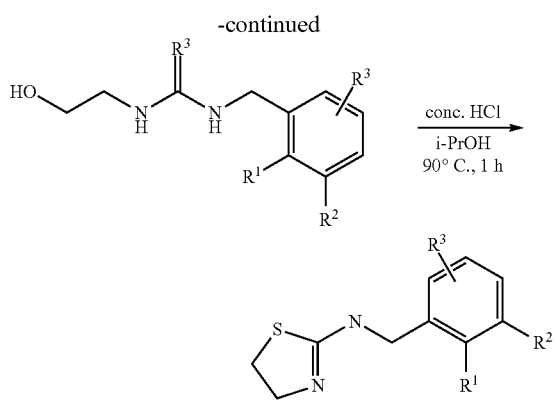

Scheme B depicts a general method for obtaining N-(Substituted benzyl)-4,5-dihydro-thiazol-2-amines.

EXAMPLE 2A

Synthesis of N-(2-methoxybenzyl)-4,5-dihydrothiazol-2-amine

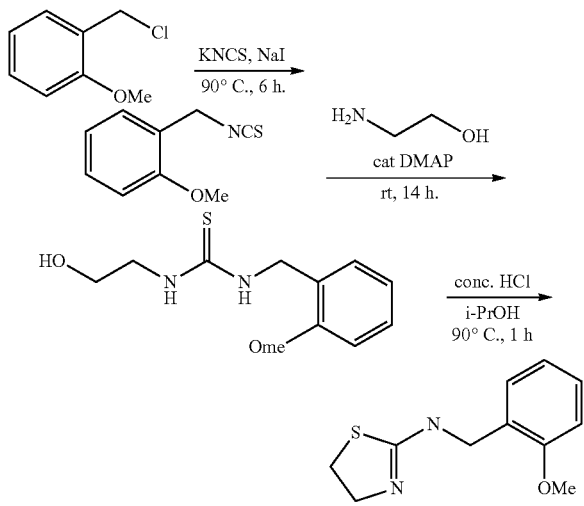

2-Methoxybenzyl chloride (30.00 mL, 170.27 mmol), KNCS (33.00 g, 340.55 mmol) and NaI (12.76 g, 85.14 mmol) were mixed in DMF (160 mL). The resulting reaction mixture was heated to 90° C. and stirred at this temperature for 6 hours, then cooled to room temperature and diluted with water (200 mL). The reaction mixture was extracted with ether (100 mL) 3 times and the combined organic phases were washed with water (200 mL) and brine (1×200 mL), then dried over $MgSO_4$ and concentrated. A portion of this crude isothiocyanate (10.00 g, 55.79 mmol) was mixed with ethanolamine (6.80 mL, 111 mmol) in acetonitrile (50 mL), a catalytic amount of DMAP (50 mg) was added. The reaction mixture was stirred at room temperature for 14 hours and then concentrated. Purification by column chromatography using hexane:EtOAc (1:1) then MeOH/EtOAc (1:10) as eluants afforded 10.41 g of the intermediate thiourea. A portion of this thiourea (2.00 g, 8.32 mmol) was dissolved in a solution of concentrated HCl (25 mL) and isopropanol (25 mL). This reaction mixture was heated to 90° C. and stirred at this temperature for 60 minutes, then cooled. Ammonium hydroxide was added to the reaction mixture to pH=13. The resulting mixture was extracted with ethyl acetate and the combined organic phases were dried over magnesium sulfate and concentrated. Crystallization from hexane gave N-(2-methoxybenzyl)-4,5-dihydrothiazol-2-amine. Spectroscopic data: $^1$H NMR (300 MHz, DMSO-d6) δ 3.23 (t, 2H, J=9.1 Hz), 3.78 (s, 3H), 3.80 (t, 2H, J=9.1 Hz), 4.34 (s, 2H), 6.86-6.96 (m, 2H), 7.18-7.25 (m, 2H).

The following compounds were prepared according to Scheme B:

N-(3-chloro-2-fluorobenzyl)-4,5-dihydrothiazol-2-amine: $^1$H NMR (300 MHz, CDCl$_3$) δ ppm 3.36 (t, J=7.33 Hz, 2 H), 3.99 (t, J=7.33 Hz, 2 H), 4.55 (s, 2 H), 6.98-7.13 (m, 1 H), 7.27-7.37 (m, 2 H).

N-(2,3-dichlorobenzyl)-4,5-dihydrothiazol-2-amine: $^1$H NMR (300 MHz, CDCl$_3$)) δ ppm 3.36 (t, J=7.33 Hz, 2 H), 3.99 (t, J=7.33 Hz, 2 H), 4.59 (s, 2 H), 7.16-7.23 (m, 1 H), 7.36 (ddd, J=15.05, 7.80, 1.47 Hz, 2 H).

N-(2-chloro-3-trifluoromethylbenzyl)-4,5-dihydrothiazol-2-amine: $^1$H NMR (500 MHz, CDCl$_3$) δ ppm 3.37 (t, J=7.32 Hz, 2 H), 3.98 (t, J=7.32 Hz, 2 H), 4.62 (s, 2H), 7.35 (t, J=7.75 Hz, 1 H), 7.63 (dd, J=7.75, 2.14 Hz, 2 H).

N-(3-Bromo-2-fluoro-5-methylbenzyl)-4,5-dihydrothiazol-2-amine: $^1$H NMR (500 MHz, CDCl$_3$) δ ppm 3.37 (t, J=7.32 Hz 2 H), 3.98 (t, J=7.32 Hz, 2 H), 4.62 (s, 2H), 7.35 (t, J=7.75 Hz, 1 H), 7.63 (dd, J=7.75, 2.14 Hz, 2 H).

N-(2-Bromo-5-chlorobenzyl)-4,5-dihydrothiazol-2-amine: $^1$H NMR (500 MHz, CDCl$_3$) δ=ppm 3.38 (t, 2 H), 4.00 (t, J=7.38 Hz, 2 H), 4.52 (s, 2 H), 7.13 (dd, J=8.42, 2.56 Hz, 1 H), 7.42 (d, J=2.56 Hz, 1 H), 7.46 (d, J=8.54 Hz, 1 H).

N-(5-Chloro-2-fluoro-3-methylbenzyl)-4,5-dihydrothiazol-2-amine: $^1$H NMR (500 MHz, CDCl$_3$) δ=ppm 2.24 (s, 3 H), 3.35 (t, J=7.32 Hz, 2 H), 3.98 (t, J=7.32 Hz, 2 H), 4.47 (s, 2 H), 7.07 (dd, J=6.22, 2.44 Hz, 1 H), 7.17 (dd, J=5.92, 2.50 Hz, 1 H).

N-(2-Chlorobenzyl)-4,5-dihydrothiazol-2-amine: $^1$H NMR (500 MHz, CDCl$_3$) δ=ppm 3.35 (t, J=7.32 Hz, 2 H), 4.00 (t, J=7.38 Hz, 2 H), 4.57 (s, 2 H), 7.20-7.27 (m, 2 H), 7.36 (dd, J=7.51, 1.65 Hz, 1 H), 7.40-7.43 (my 1 H).

N-(5-Bromo-2-chlorobenzyl)-4,5-dihydrothiazol-2-amine: $^1$H NMR (500 MHz, CDCl$_3$) δ=ppm 3.38 (t, J=7.32 Hz, 2 H), 3.99 (t, J=7.32 Hz, 2 H), 4.54 (s, 2 H), 7.22 (d, 54.42 Hz, 1 H), 7.34 (dd, J=8.48, 2.38 Hz, 1 H), 7.56 (d, J=2.32 Hz, 1 H).

N-(3-Chloro-2-methoxybenzyl)-4,5-dihydrothiazol-2-amine: $^1$H NMR (500 MHz, CDCl$_3$) δ=ppm 3.31-3.37 (m, 2 H), 3.89 (d, J=1.71 Hz, 3 H), 4.00 (t, J=7.32 Hz, 2 H), 4.53 (s, 2 H), 7.01-7.06 (m, 1 H), 7.26 (d, J=7.81 Hz, 1 H), 7.30 (d, J=8.06 Hz, 1 H).

N-(2-Methoxy-3-methylbenzyl)-4,5-dihydrothiazol-2-amine: $^1$H NMR (500 MHz, CDCl$_3$) δ=ppm 2.31 (s, 3 H), 3.34 (t, J=7.32 Hz, 2 H), 3.77 (s, 3 H), 4.03 (t, J=7.32 Hz, 2 H), 4.53 (s, 2 H), 6.98-7.03 (m, 1 H), 7.12 (d, J=7.32 Hz, 1 H), 7.18 (d, J=7.32 Hz, 1 H).

N-(2-Chloro-3-methylbenzyl)-4,5-dihydrothiazol-2-amine: $^1$H NMR (500 MHz, CDCl$_3$) δ=ppm 2.39 (s, 3 H), 3.35 (t, J=7.32 Hz, 2 H), 4.01 (t, J=7.45 Hz, 2 H), 4.58 (s, 2 H), 7.15 (m, 1 H), 7.17 (m, 1 H), 7.24-7.27 (m, 1 H).

N-(3-Bromo-2-methoxybenzyl)-4,5-dihydrothiazol-2-amine: $^1$H NMR (500 MHz, CDCl$_3$) δ ppm 3.34 (t, J=7.32 Hz, 2 H), 3.87 (s, 3 H), 4.00 (t, J=7.32 Hz, 2 H), 4.55 (s, 2 H), 6.98 (t, J=7.69 Hz, 1 H), 7.30 (d, J=7.57 Hz, 1 H), 7.47 (d, J=8.06 Hz, 1 H).

N-(3-Chloro-2-methylbenzyl)-4,5-dihydrothiazol-2-amine: $^1$H NMR (500 MHz, CDCl$_3$) δ=ppm 2.38 (s, 3 H), 3.36 (t, J=7.38 Hz, 2 H), 4.01 (t, J=7.32 Hz, 2 H), 4.48 (s, 2 H), 7.08-7.13 (m, 1 H), 7.19 (d, J=7.45 Hz, 1 H), 7.31 (d, J=7.93 Hz, 1 H)

N-(3-Bromo-2-chlorobenzyl)-4,5-dihydrothiazol-2-amine: $^1$H NMR (300 MHz, CDCl$_3$) δ=ppm 3.35 (t, J=7.40 Hz, 2 H), 3.98 (t, J=7.33 Hz, 2 H), 4.59 (s, 2 H), 7.07-7.16 (m, 1 H), 7.38 (d, J=7.48 Hz, 1 H), 7.55 (dd, J=7.92, 1.32 Hz, 1 H).

N-(2-Bromo-3-chlorobenzyl)-4,5-dihydrothiazole-2-amine: $^1$H NMR (300 MHz, CDCl$_3$) δ=ppm 3.36 (t, J=7.33 Hz, 2 H), 3.99 (t, J=7.33 Hz, 2 H), 4.58 (s, 2 H), 7.20-7.26 (m, 1 H), 7.30-7.35 (m, 1 H), 7.39 (dd, J=7.77, 1.76 Hz, 1 H).

N-(2-Fluoro-3-iodobenzyl)-4,5-dihydrothiazol-2-amine: $^1$H NMR (300 MHz, CDCl$_3$) δ=ppm 3.29-3.42 (m, 2 H), 4.00 (t, J=7.33 Hz, 2 H), 4.55 (s, 2 H), 6.89 (t, J=7.77 Hz, 1 H), 7.36 (t, J=7.26 Hz, 1 H), 7.66 (dd, J=7.26, 6.52 Hz, 1 H).

N-(2-Bromobenzyl)-4,5-dihydrothiazol-2-amine: $^1$H NMR (500 MHz, CDCl$_3$) δ=ppm 3.36 (t, J=7.38H, 2 H), 4.01 (t, J=7.38 Hz, 2 H), 4.56 (s, 2 H), 7.15 (td, J=7.63, 1.46 Hz, 1 H), 7.30 (t, J=7.44 Hz, 1 H), 7.42 (dd, J=7.63, 1.04 Hz, 1 H), 7.55 (d, J=7.93 Hz, 1 H).

N-(2-Fluoro-3-trifluoromethylbenzyl)-4,5-dihydrothiazol-2-amine: $^1$H NMR (500 MHz, CDCl$_3$) δ=ppm 3.35 (t, J=7.32 Hz, 2 H), 3.97 (t, J=7.32 Hz, 2 H), 4.57 (s, 2 H), 7.21 (t, J=7.75 Hz, 1 H), 7.51 (t, J=7.32 Hz, 1 H), 7.61 (t, 1 H).

N-(3-Chlorobenzyl)-4,5-dihydrothiazol-2-amine: $^1$H NMR (500 MHz, CDCl$_3$) δ ppm 3.37 (t, J=7.38 Hz, 2 H), 4.00 (t, J=7.32 Hz, 2 H), 4.47 (s, 2 H), 7.18-7.22 (m, 1H), 7.22-7.26 (m, 2 H), 7.32 (s, 1 H).

N-(3-Bromobenzyl)-4,5-dihydrothiazol-2-amine: $^1$H NMR (500 MHz, CDCl$_3$) δ ppm 3.37 (t, J=7.38 Hz, 2 H), 3.49 (s, 1 H), 4.00 (t, J=7.32 Hz, 2 H), 4.47 (s, 2 H), 7.18-7.23 (m, 1 H), 7.24-7.27 (m, 1 H), 7.41 (d, J=7.81 Hz, 1 H), 7.48 (s, 1H).

N-(3-Bromo-2-fluorobenzyl)-4,5-dihydrothiazol-2-amine: $^1$H NMR (500 MHz, CDCl$_3$) δ=ppm 3.36 (t, J=7.38 Hz, 2 H), 3.98 (t, J=7.32 Hz, 2 H), 4.55 (s, 2 H), 7.00 (t, J=7.81 Hz, 1 H), 7.33 (t, J=6.35 Hz, 1 H), 7.43-7.49 (m, 1 H).

N-(5-Chloro-2-methoxybenzyl)-4,5-dihydrothiazol-2-amine: $^1$H NMR (500 MHz, CDCl$_3$) δ=ppm 3.35 (t, J=7.38 Hz, 2 H), 3.83 (s, 3 H), 4.01 (t, J=7.38 Hz, 2 H), 4.44 (s, 2 H), 6.78 (d, J=8.67 Hz, 1 H), 7.20 (dd, J=8.67, 2.56 Hz, 1 H), 7.28 (d, J=2.69 Hz, 1 H).

N-(2-Bromo-5-fluorobenzyl)-4,5-dihydrothiazol-2-amine: $^1$H NMR (500 MHz, CDCl$_3$,) δ=ppm 3.38 (t, J=7.38 Hz, 2 H), 3.99 (t, J=7.38 Hz, 2 H), 4.52 (s, 2 H), 6.87 (td, J=8.30, 3.05 Hz, 1 H), 7.17 (dd, J=9.28, 3.05 Hz, 1 H), 7.49 (dd, J=8.79, 5.25 Hz, 1 H).

N-(5-Bromo-2-fluorobenzyl)-4,5-dihydrothiazol-2-amine: $^1$H NMR (500 MHz, CDCl$_3$) δ=ppm 3.37 (t, J=7.38 Hz, 2 H), 3.99 (t, J=7.32 Hz, 2 H), 4.51 (s, 2 H), 6.93 (t, J=9.09 Hz, 1 H), 7.36 (ddd, J=8.60, 4.58, 2.56 Hz, 1 H), 7.52 (dd, J=6.59, 2.44 Hz, 1 H).

EXAMPLE 3

RSAT Assay

Selected presently described compounds were synthesized and tested for alpha adrenergic activity using the Receptor Selection and Amplification Technology (RSAT) assay. Cells expressing each of the alpha-2-adrenergic receptors alone were incubated with various compounds and a receptor-mediated growth response was measured. The compound's activity is expressed as its relative efficacy compared to a standard full agonist. Presently described compounds activate alpha2B and/or alpha2C receptors.

The RSAT assay measures a receptor-mediated loss of contact inhibition that results in selective proliferation of receptor-containing cells in a mixed population of confluent cells. The increase in cell number is assessed with an appropriate transfected marker gene such as .beta.-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-.beta.-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μg added to 100 μg aliquots of various concentrations of drugs in triplicate in 96-well dishes. Incubations continue 72-96 hr at 37° C. After washing with phosphatebuffered saline, .beta.-galactosidase enzyme activity is determined by adding 200 μl of the chromogenic substrate (consisting of 3.5 mM o-nitrophenyl-.beta.-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The EC$_{50}$ and maximal effect of each drug at each alpha.sub.2 receptor is determined. The efficacy or intrinsic activity is calculated as a ratio of the maximal effect of the drug to the maximal effect of a standard full agonist for each receptor subtype. Brimonidine, also called UK14304, is used as the standard agonist for the alpha2A, alpha2B, and alpha2C receptors.

Example compounds of the present disclosure are disclosed by their structural formulas in the following table together with their potency expressed in nanomolar (nM) as the concentration at which half of their maximal activity is observed (EC$_{50}$). The compounds activity is expressed as its relative efficacy compared to a standard full agonist.

TABLE 1

Compound Activity Expressed as Its Relative Efficacy Compared to Standard Full Agonist.

| STRUCTURE | Biological Data EC$_{50}$ (nM) (rel. efficacy) NA = not active | | |
|---|---|---|---|
| | Alpha 2A | Alpha 2B | Alpha 2C |
| (structure) | NA | NA | 1553 (0.74) |

TABLE 1-continued

Compound Activity Expressed as Its Relative Efficacy Compared to Standard Full Agonist.

| STRUCTURE | Biological Data EC$_{50}$ (nM) (rel. efficacy) NA = not active | | |
|---|---|---|---|
| | Alpha 2A | Alpha 2B | Alpha 2C |
| (oxazoline-NH-CH2-C6H4-2-OCH3) | NA | 13.4 (1.09) | 180.8 (0.53) |
| (thiazoline-NH-CH2-C6H3-2-F-3-Cl) | NA | 107 (1.01) | 535 (0.7) |
| (oxazoline-NH-CH2-C6H3-2-F-3-Cl) | NA | 10 (1.09) | 22 (0.85) |
| (thiazoline-NH-CH2-C6H3-2-F-3-CF3) | NA | 184 (0.99) | 1430 (0.73) |
| (thiazoline-NH-CH2-C6H4-2-Br) | 2780 (0.37) | 29 (0.84) | 190 (0.77) |
| (thiazoline-NH-CH2-C6H4-3-Cl) | NA | 42 (0.99) | 504 (0.48) |
| (thiazoline-NH-CH2-C6H4-3-Br) | NA | 75 (0.84) | 459 (0.5) |
| (thiazoline-NH-CH2-C6H3-2-F-3-Br) | 1377 (0.44) | 34 (0.98) | 182 (0.64) |
| (thiazoline-NH-CH2-C6H3-2-OCH3-5-Cl) | 2253 (0.38) | 77 (0.85) | 465 (0.55) |
| (thiazoline-NH-CH2-C6H3-2-Br-5-F) | NA | 73 (0.97) | 452 (0.67) |
| (thiazoline-NH-CH2-C6H3-2-F-5-Br) | NA | 280 (0.85) | 2060 (0.64) |
| (thiazoline-NH-CH2-C6H3-2,3-Cl2) | NA | 28 (0.94) | 252 (0.68) |
| (thiazoline-NH-CH2-C6H3-2-Cl-3-CF3) | NA | 101 (1.08) | 854 (0.46) |
| (thiazoline-NH-CH2-C6H2-2-F-3-Br-5-CH3) | NA | 168 (1.04) | 803 (0.62) |
| (thiazoline-NH-CH2-C6H3-2-Br-5-Cl) | 2266 (0.45) | 250 (1.04) | 855 (0.69) |

TABLE 1-continued

Compound Activity Expressed as Its Relative Efficacy Compared to Standard Full Agonist.

| STRUCTURE | Biological Data EC$_{50}$ (nM) (rel. efficacy) NA = not active | | |
|---|---|---|---|
| | Alpha 2A | Alpha 2B | Alpha 2C |
| 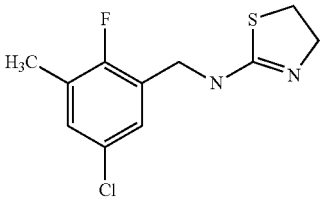 | NA | 351 (0.96) | 1254 (0.51) |
| 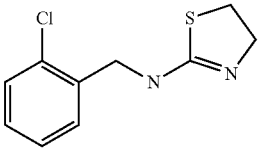 | NA | 50 (0.85) | 699 (0.66) |
| 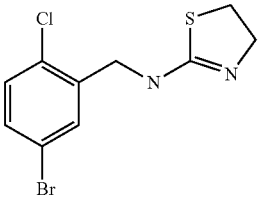 | NA | 296 (0.9) | 1326 (0.56) |
| 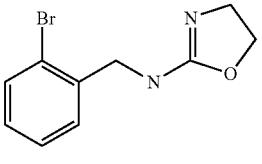 | NA | 5 (1.09) | 85 (0.85) |
| 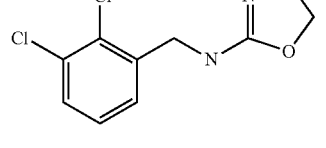 | NA | 5 (1.05) | 92 (0.91) |
| 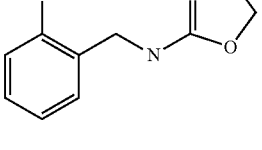 | NA | 3.3 (1.02) | 42 (0.83) |
| 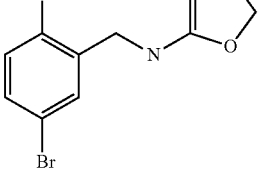 | NA | 20 (0.98) | 81 (0.71) |

TABLE 1-continued

Compound Activity Expressed as Its Relative Efficacy Compared to Standard Full Agonist.

| STRUCTURE | Biological Data EC$_{50}$ (nM) (rel. efficacy) NA = not active | | |
|---|---|---|---|
| | Alpha 2A | Alpha 2B | Alpha 2C |
| 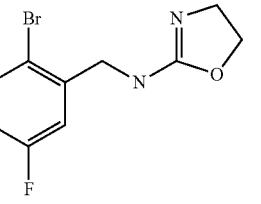 | NA | 4 (1.05) | 29 (0.71) |
| 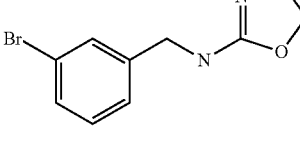 | NA | 12 (1.0) | 83 (0.59) |
| 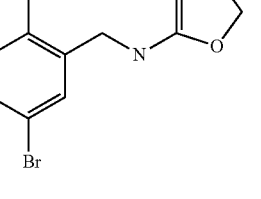 | NA | 18 (0.89) | 186 (0.63) |
| 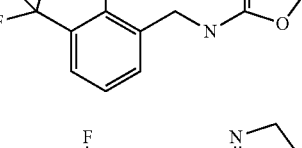 | NA | 5 (0.96) | 189 (0.81) |
| 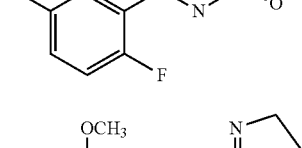 | NA | 57 (0.93) | 356 (0.52) |
| 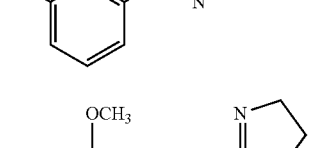 | 701 (0.38) | 22 (1.08) | 99 (0.73) |
| 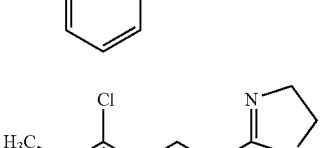 | 481 (0.57) | 27 (0.98) | 187 (0.97) |
| 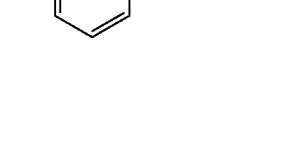 | 281 (0.4) | 11 (1.27) | 32 (1.03) |

TABLE 1-continued

Compound Activity Expressed as Its Relative Efficacy Compared to Standard Full Agonist.

| STRUCTURE | Biological Data EC$_{50}$ (nM) (rel. efficacy) NA = not active | | |
|---|---|---|---|
| | Alpha 2A | Alpha 2B | Alpha 2C |
| (OCH3, Br — benzyl — dihydrothiazol-2-amine) | 621 (0.55) | 31 (1.1) | 109 (0.81) |
| (CH3, Cl — benzyl — dihydrothiazol-2-amine) | NA | 40 (0.99) | 401 (0.72) |
| (Cl, Br — benzyl — dihydrothiazol-2-amine) | >3000 (0.4) | 18 (1.01) | 198 (0.98) |
| (Br, Cl — benzyl — dihydrothiazol-2-amine) | NA | 40 (0.85) | 303 (0.68) |
| (F, I — benzyl — dihydrothiazol-2-amine) | 589 (1.07) | 6 (1.0) | 88 (1.05) |
| (H3C, CH3 — benzyl — dihydrooxazol-2-amine) | NA | 2 (1.09) | 11 (0.83) |
| (OCHF2 — benzyl — dihydrooxazol-2-amine) | NA | 34 (0.83) | 13 (0.74) |
| (CF3 — benzyl — dihydrooxazol-2-amine) | NA | 31 (0.97) | 21 (0.8) |
| (OCHF2 meta — benzyl — dihydrooxazol-2-amine) | NA | 217 (0.6) | 60 (0.49) |
| (F meta — benzyl — dihydrooxazol-2-amine) | NA | 39 (0.82) | 17 (0.59) |

EXAMPLE 4

Treating Elevated Intraocular Disease

I. A patient exhibits moderate intraocular pressure in the right eye. An ophthalmic composition including N-(2-methoxybenzyl)-4,5-dihydrooxazol-2-amine is delivered to the right eye of the patient twice daily. Two months later, the patient exhibits normal intraocular pressure.

II. A patient exhibits moderate intraocular pressure in the right eye. An ophthalmic composition including N-(2-methoxybenzyl)-4,5-dyhydrothizaol-2-amine is delivered to the right eye of the patient twice daily. Two months later, the patient exhibits normal intraocular pressure.

III. A patient exhibits moderate intraocular pressure in the right eye. An ophthalmic composition including N-(3-chloro-2-fluorobenzyl)-4,5-dihydrooxazol-2-amine is delivered to the right eye of the patient twice daily. Two months later, the patient exhibits normal intraocular pressure.

EXAMPLE 5

Treating Post-Herpetic Neuralgia Pain

I. A patient exhibits moderate post-herpetic neuralgia pain. A tablet including N-(2-methoxybenzyl)-4,5-dihydrooxazol-2-amine is delivered taken by the patient twice daily as needed for the pain. The patient reports a reduction of pain when taking the tablet.

II. A patient exhibits moderate post-herpetic neuralgia pain. A tablet including N-(2-methoxybenzyl)-4,5-dyhydrothizaol-2-amine is delivered taken by the patient twice daily as needed for the pain. The patient reports a reduction of pain when taking the tablet.

III. A patient exhibits moderate post-herpetic neuralgia pain. A tablet including N-(3-chloro-2-fluorobenzyl)-4,5-dihydrooxazol-2-amine is delivered taken by the patient twice daily as needed for the pain. The patient reports a reduction of pain when taking the tablet.

EXAMPLE 6

Treating Diabetic Peripheral Neuropathy

I. A diabetic patient exhibits moderate neuropathy in the right leg. A topical composition including N-(2-methoxybenzyl)-4,5-dihydrooxazol-2-amine is administered on the right leg of the patient twice daily. Two months later, the patient exhibits a reduction neuropathy.

III. A diabetic patient exhibits moderate neuropathy in the right leg. A topical composition including N-(2-methoxybenzyl)-4,5-dyhydrothizaol-2-amine is administered on the right leg of the patient twice daily. Two months later, the patient exhibits a reduction neuropathy.

III. A diabetic patient exhibits moderate neuropathy in the right leg. A topical composition including N-(3-chloro-2-fluorobenzyl)-4,5-dihydrooxazol-2-amine is administered on the right leg of the patient twice daily. Two months later, the patient exhibits a reduction neuropathy.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. A compound selected from:

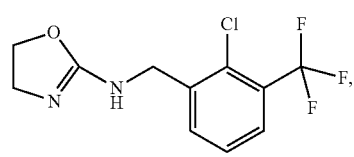

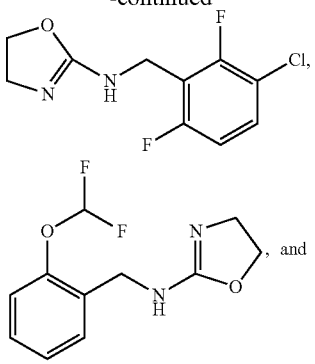
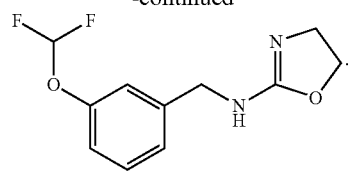
2. A pharmaceutical composition comprising at least one a compound according to claim 1 in a pharmaceutically acceptable carrier.
* * * * *

UNITED STATES PATENT AND TRADEMARK OFFICE
CERTIFICATE OF CORRECTION

PATENT NO. : 8,329,918 B2
APPLICATION NO. : 12/828429
DATED : December 11, 2012
INVENTOR(S) : Phong X. Nguyen et al.

It is certified that error appears in the above-identified patent and that said Letters Patent is hereby corrected as shown below:

In column 2, line 50, delete "N(R$^5$)2," and insert -- N(R$^5$)$_2$, --, therefor.
In column 6, line 62, delete "neurodegerative" and insert -- neurodegenerative --, therefor.
In column 7, line 20, delete "(—C(O)" and insert -- (—OC(O) --, therefor.
In column 9, line 28, delete "N(R$^5$)2," and insert -- N(R$^5$)$_2$, --, therefor.
In column 13, line 56, delete "neurodegerative" and insert -- neurodegenerative --, therefor.
In column 13, line 59, delete "Guillan-Barre" and insert -- Guillain-Barre --, therefor.
In column 13, line 67, delete "chromic" and insert -- chronic --, therefor.
In column 15, line 53, delete "ophthalmic ally" and insert -- ophthalmically --, therefor.
In column 16, line 44, after "practitioner" insert -- . --.
In column 18, line 1, delete "fluorobenzyl)" and insert -- fluoro benzyl) --, therefor.

In column 19, line 40, delete " 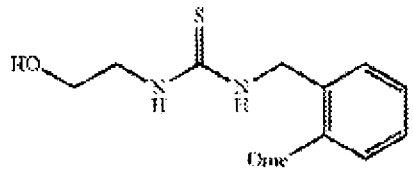 " and insert -- 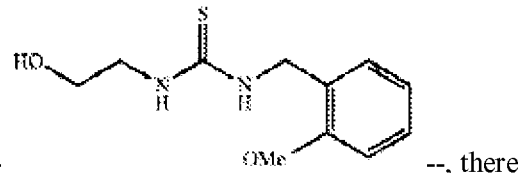 --, therefor.

In column 21, line 3, after "1 H)" insert -- . --.
In column 21, line 18, delete "7.38H," and insert -- 7.38 Hz, --, therefor.
In column 28, line 45, delete "dyhydrothizaol" and insert -- dihydrothiazol --, therefor.
In column 28, lines 64-65, delete "dyhydrothizaol" and insert -- dihydrothiazol --, therefor.
In column 29, line 17, delete "III." and insert -- II. --, therefor.
In column 29, line 19, delete "dyhydrothizaol" and insert -- dihydrothiazol --, therefor.
In column 32, line 10, in claim 2, after "one" delete "a".

Signed and Sealed this
Ninth Day of April, 2013

Teresa Stanek Rea
*Acting Director of the United States Patent and Trademark Office*